United States Patent
Agarwal et al.

(10) Patent No.: US 12,257,139 B2
(45) Date of Patent: Mar. 25, 2025

(54) PROTECTIVE CONTAINER FOR STERILIZED MEDICAL IMPLANTS

(71) Applicant: Guardian Medical USA, LLC, Swanton, OH (US)

(72) Inventors: Aakash Agarwal, Swanton, OH (US); Tracy Momany, Swanton, OH (US)

(73) Assignee: GUARDIAN MEDICAL USA, INC., Swanton, OH (US)

( * ) Notice: Subject to any disclaimer, the term of this patent is extended or adjusted under 35 U.S.C. 154(b) by 1109 days.

(21) Appl. No.: 16/970,230

(22) PCT Filed: Feb. 15, 2019

(86) PCT No.: PCT/US2019/018201
§ 371 (c)(1),
(2) Date: Aug. 14, 2020

(87) PCT Pub. No.: WO2019/161186
PCT Pub. Date: Aug. 22, 2019

(65) Prior Publication Data
US 2021/0077242 A1  Mar. 18, 2021

Related U.S. Application Data

(60) Provisional application No. 62/630,997, filed on Feb. 15, 2018.

(51) Int. Cl.
*A61F 2/00* (2006.01)
*A61B 50/00* (2016.01)
(Continued)

(52) U.S. Cl.
CPC ............ *A61F 2/0095* (2013.01); *A61B 50/00* (2016.02); *A61L 2/206* (2013.01); *A61L 2/26* (2013.01);
(Continued)

(58) Field of Classification Search
CPC .................. A61F 2/0095; A61B 50/00; A61B 2050/0064; A61B 2050/0066;
(Continued)

(56) References Cited

U.S. PATENT DOCUMENTS 3,602,238 A * 8/1971 Brown ................. G02C 13/008
220/500
4,322,011 A * 3/1982 Mumford ........... B65D 41/0414
215/270
(Continued)

FOREIGN PATENT DOCUMENTS

WO 2018009401 A1 1/2018

OTHER PUBLICATIONS

Chinese First Office Action, Application No. 201980022907.9, dated Sep. 17, 2023.
(Continued)

*Primary Examiner* — Jacob K Ackun
(74) *Attorney, Agent, or Firm* — Michael E. Dockins; Shumaker, Loop & Kendrick LLP

(57) ABSTRACT

A protective container for a sterilized medical implant includes a base including a hollow body having a closed end and an opened end. The base including a thread. A cap is secured about the opened end of the hollow body. The cap includes a thread that cooperates with the thread provided on the base such that relative rotation of the base and the cap causes relative axial movement of the base and the cap. A sealing member is compressed between the base and the cap to provide a seal therebetween as a result of relative axial movement of the base and the cap.

7 Claims, 15 Drawing Sheets

(51) Int. Cl.
*A61L 2/20* (2006.01)
*A61L 2/26* (2006.01)

(52) U.S. Cl.
CPC ............... *A61B 2050/0064* (2016.02); *A61B 2050/0066* (2016.02); *A61L 2202/182* (2013.01); *A61L 2202/21* (2013.01)

(58) Field of Classification Search
CPC ...... A61L 2/206; A61L 2/26; A61L 2202/182; A61L 2202/21
USPC ........................................ 206/438, 440, 63.5
See application file for complete search history.

(56) References Cited

U.S. PATENT DOCUMENTS

| | | | | |
|---|---|---|---|---|
| 5,217,114 | A * | 6/1993 | Gadberry | A61M 25/002 206/439 |
| 5,269,413 | A * | 12/1993 | Stern | B65D 83/04 206/811 |
| 6,006,942 | A * | 12/1999 | Morris, Sr. | B65D 21/0219 206/508 |
| 6,702,133 | B1 * | 3/2004 | Shenkar | B65D 41/045 215/354 |
| 7,790,105 | B2 | 9/2010 | Bala | |
| 8,398,615 | B2 * | 3/2013 | Torstensen | A61M 25/0111 206/438 |
| 8,839,957 | B2 * | 9/2014 | Murad | A61F 2/0095 206/363 |
| 10,398,523 | B2 * | 9/2019 | Roesler | A61C 8/0087 |
| 11,129,689 | B2 * | 9/2021 | Peterson | A61B 17/865 |
| 11,622,574 | B2 * | 4/2023 | Awuondo | A24F 15/12 206/85 |
| 2002/0125205 | A1 * | 9/2002 | Hathaway | B65D 39/082 220/304 |
| 2006/0113207 | A1 * | 6/2006 | Ryan | A61F 2/0095 623/2.1 |
| 2007/0000801 | A1 * | 1/2007 | Mauran | A61F 2/167 206/438 |
| 2007/0193905 | A1 * | 8/2007 | Jemelin | A61B 50/3001 206/438 |
| 2011/0147251 | A1 * | 6/2011 | Hodshon | A61F 2/2412 206/438 |
| 2012/0245535 | A1 | 9/2012 | Jacobsson et al. | |
| 2012/0290079 | A1 * | 11/2012 | Murad | A61F 2/2412 623/2.17 |
| 2014/0042050 | A1 * | 2/2014 | Richart | A61F 2/0095 206/438 |
| 2014/0127645 | A1 * | 5/2014 | Goldenberg | A61B 17/86 606/301 |
| 2016/0001058 | A1 * | 1/2016 | Ziebol | A61M 25/0017 206/438 |
| 2017/0095308 | A1 | 4/2017 | Roesler et al. | |

OTHER PUBLICATIONS

The extended European Search Report, Application No. 19754501.5, dated Feb. 11, 2022.

\* cited by examiner

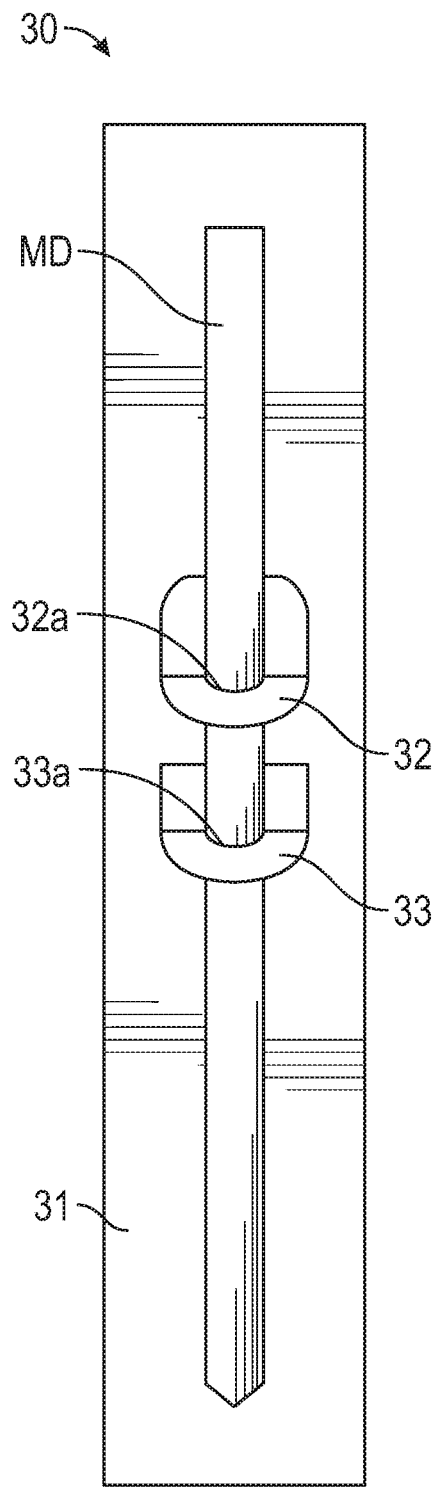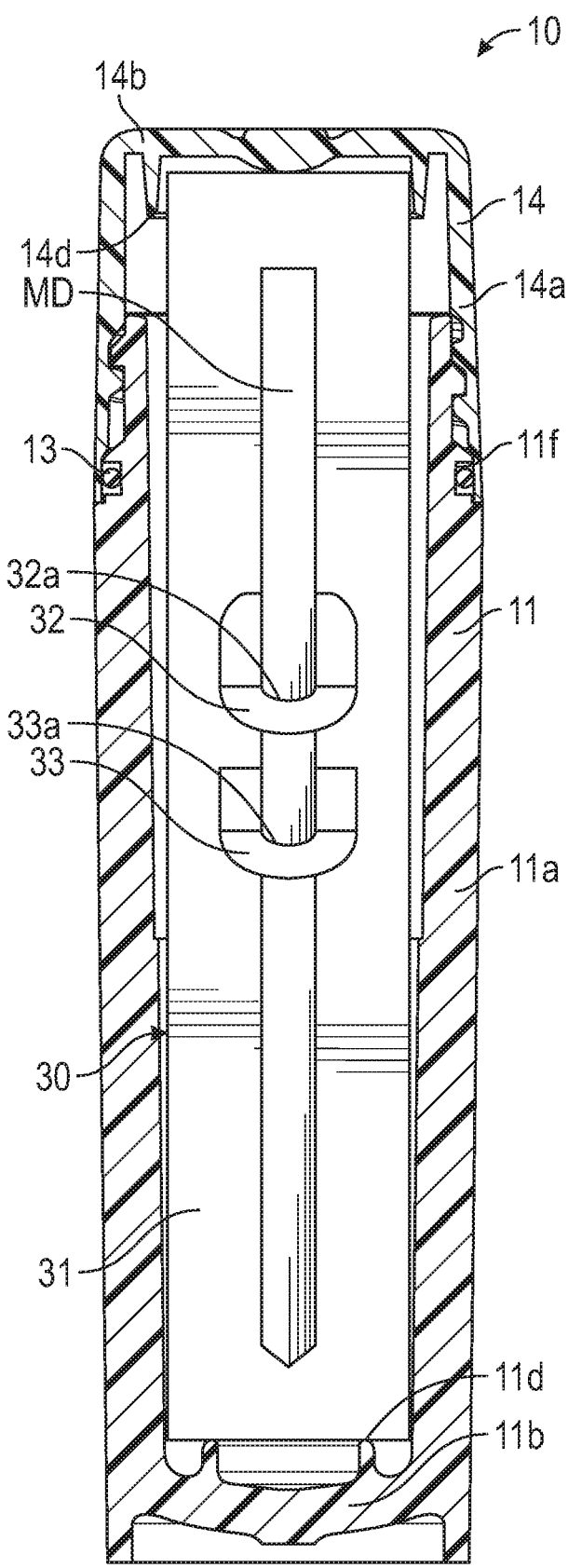
FIG. 7
FIG. 8

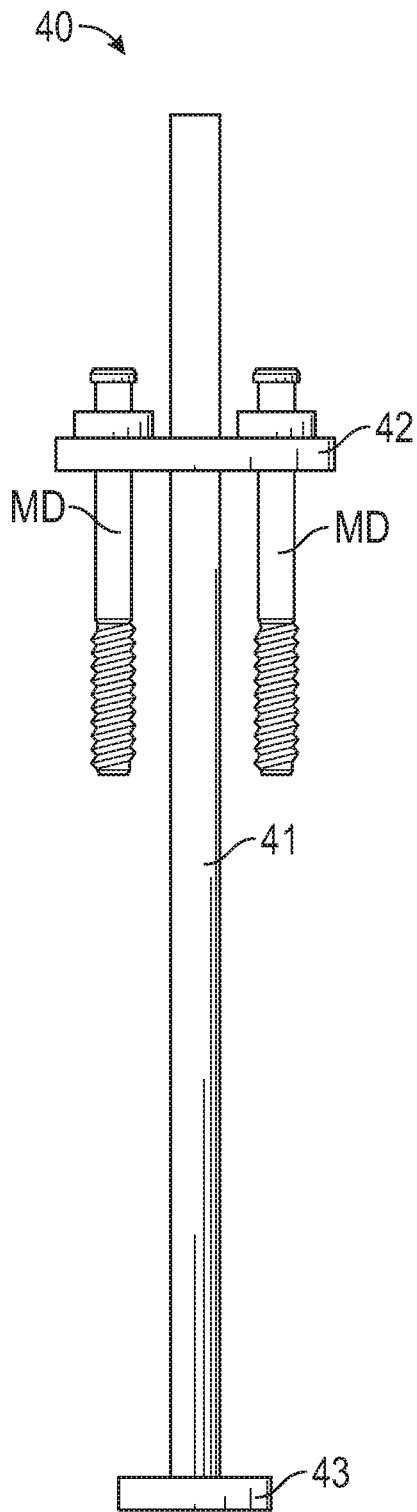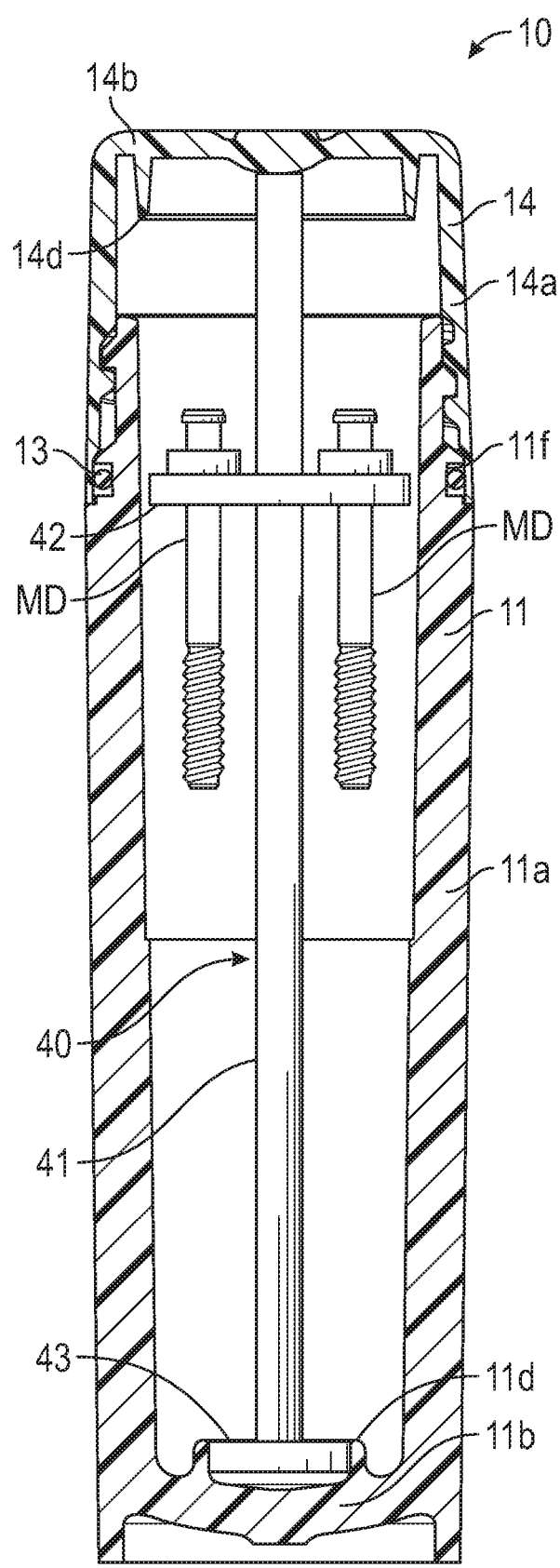
FIG. 9
FIG. 10

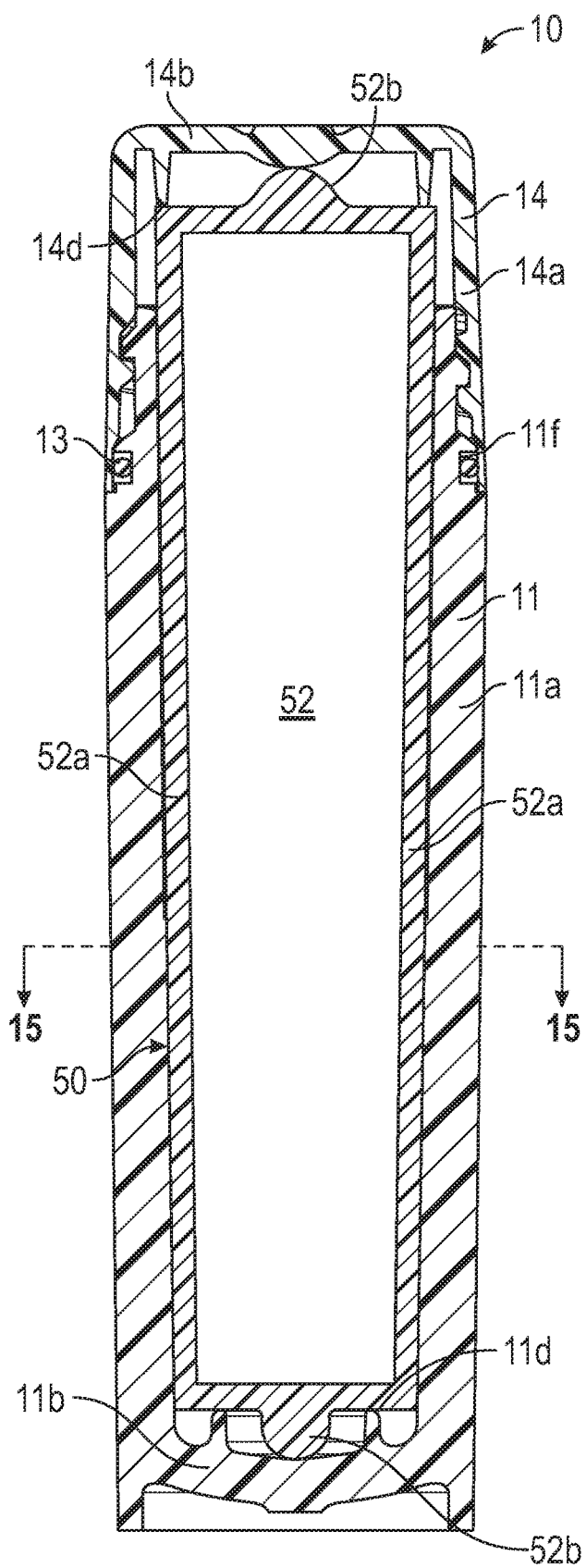
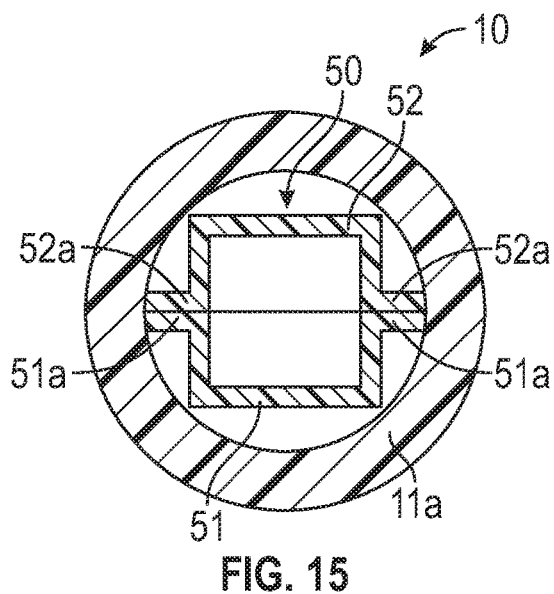
FIG. 14
FIG. 15

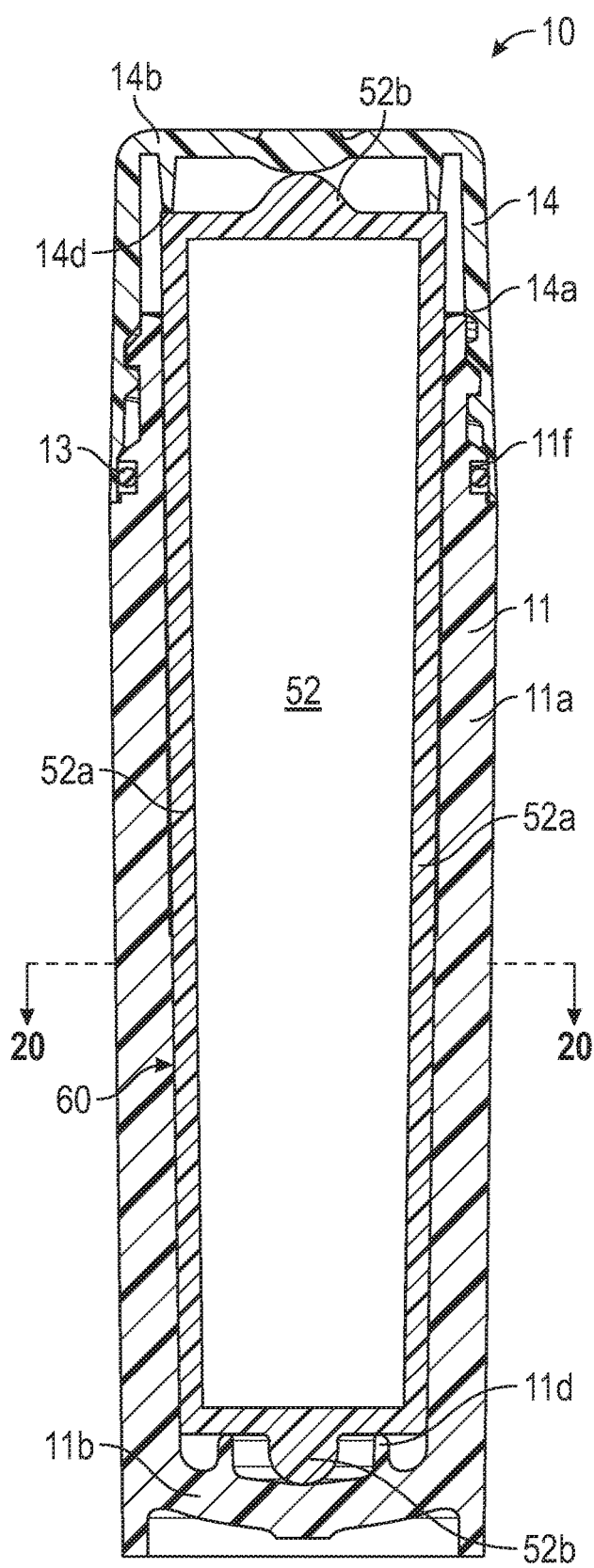
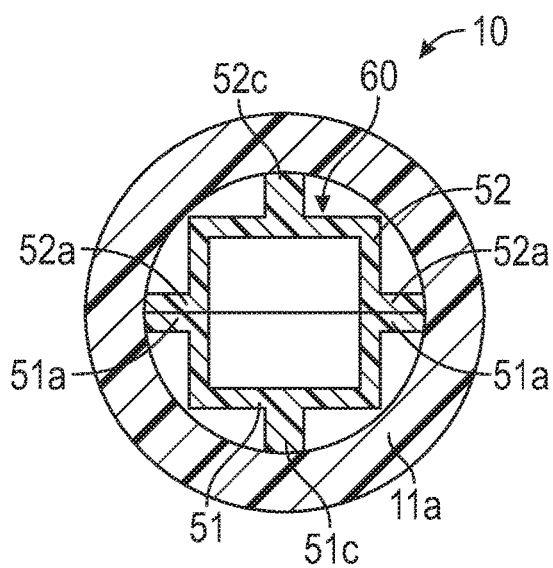
FIG. 19
FIG. 20

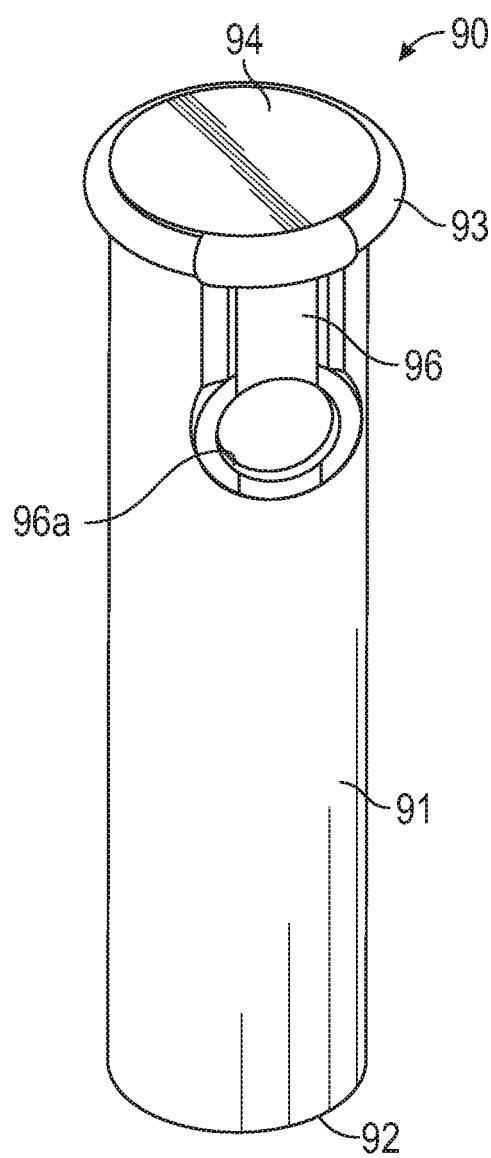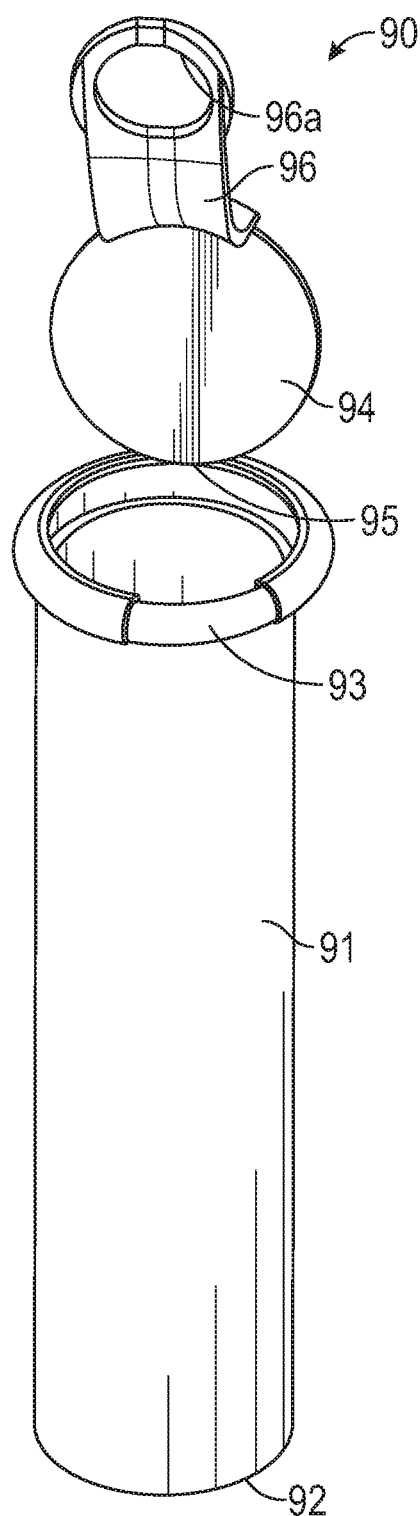
FIG. 24
FIG. 25

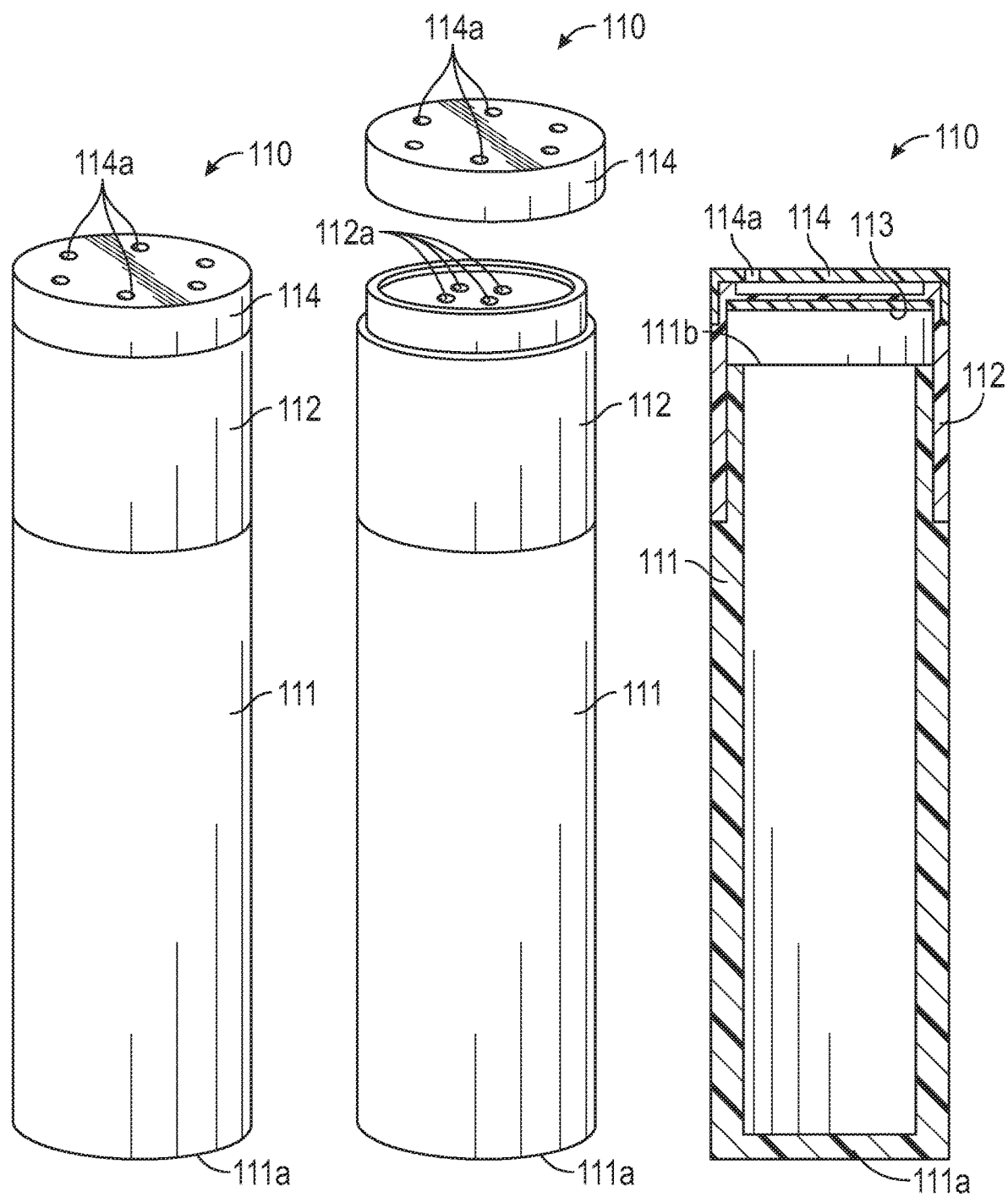

PROTECTIVE CONTAINER FOR STERILIZED MEDICAL IMPLANTS

CROSS-REFERENCE TO RELATED APPLICATIONS

This application claims the benefit of U.S. Provisional Application No. 62/630,997, filed Feb. 15, 2018, the disclosure of which is incorporated herein by reference.

BACKGROUND OF THE INVENTION

This invention relates in general to medical implants and other medical devices. In particular, this invention relates to an improved structure for a protective container for supporting a sterilized medical implant to prevent exposure to contaminants prior to installation in a human or animal body during a surgical procedure.

The current state of art in medical device sterile packaging is limited to blister packs, trays, pouches, and tubes relying on plug seals. The disadvantages of these known structures include cumbersome manufacturing processes, low performance sealing, poor stability during transportation, and subpar time and technique for sterile transfer. Therefore, it would be advantageous to provide an improved structure for a protective container for supporting a sterilized medical implant to protect it from exposure to contaminants prior to installation in a human or animal body during a surgical procedure.

SUMMARY OF THE INVENTION

Disclosed herein is a universal packaging tube with key utility characteristics related to sealing of the tube, support for additional inner tubes, stability of the containments during transportation, and provision for superior transfer from non-sterile to sterile field. In its most basic embodiment, this invention relates to a universal tube-shaped container for sterilization and containment of sterile medical-devices, incorporating a pressure sealant, a medical device stabilizing feature, an inner holder for ergonomics and/or additional barrier during exchange between non-sterile and sterile field, and an identifying characteristics, such as see-through transparency and translucent color-coding (tinting).

Various aspects of this invention will become apparent to those skilled in the art from the following detailed description of the preferred embodiments, when read in light of the accompanying drawings.

BRIEF DESCRIPTION OF THE DRAWINGS

FIG. 7 is a side elevational view of a second embodiment of a storage device that may be used with the first embodiment of the protective container illustrated in FIGS. 1 through 4.

FIG. 8 is a sectional elevational view of the second embodiment of the device illustrated in FIG. 7 shown supported within the first embodiment of the protective container illustrated in FIGS. 1 through 4.

FIG. 9 is a side elevational view of a third embodiment of a storage device that may be used with the first embodiment of the protective container illustrated in FIGS. 1 through 4.

FIG. 10 is a sectional elevational view of the third embodiment of the storage device illustrated in FIG. 9 shown supported within the first embodiment of the protective container illustrated in FIGS. 1 through 4.

FIG. 14 is a sectional elevational view of the fourth embodiment of the storage device illustrated in FIGS. 11 through 13 shown supported within the first embodiment of the protective container illustrated in FIGS. 1 through 4.

FIG. 15 is a sectional elevational view taken along line 15-15 of FIG. 14.

FIG. 19 is a sectional elevational view of the fifth embodiment of the storage device illustrated in FIGS. 16 through 18 shown supported within the first embodiment of the protective container illustrated in FIGS. 1 through 4.

FIG. 20 is a sectional elevational view taken along line 20-20 of FIG. 19.

FIG. 24 is a perspective view of a third embodiment of a protective container in accordance with this invention, shown in a closed condition.

FIG. 25 is a perspective view of the third embodiment of the protective container illustrated in FIG. 24, shown in an opened condition.

FIG. 28 is a perspective view of a fifth embodiment of a protective container in accordance with this invention.

FIG. 29 is an exploded perspective view of the fifth embodiment of the protective container illustrated in FIG. 28.

FIG. 30 is a sectional elevational view of the fifth embodiment of the protective container illustrated in FIGS. 28 and 29.

DETAILED DESCRIPTION OF THE PREFERRED EMBODIMENTS

Figure 1:
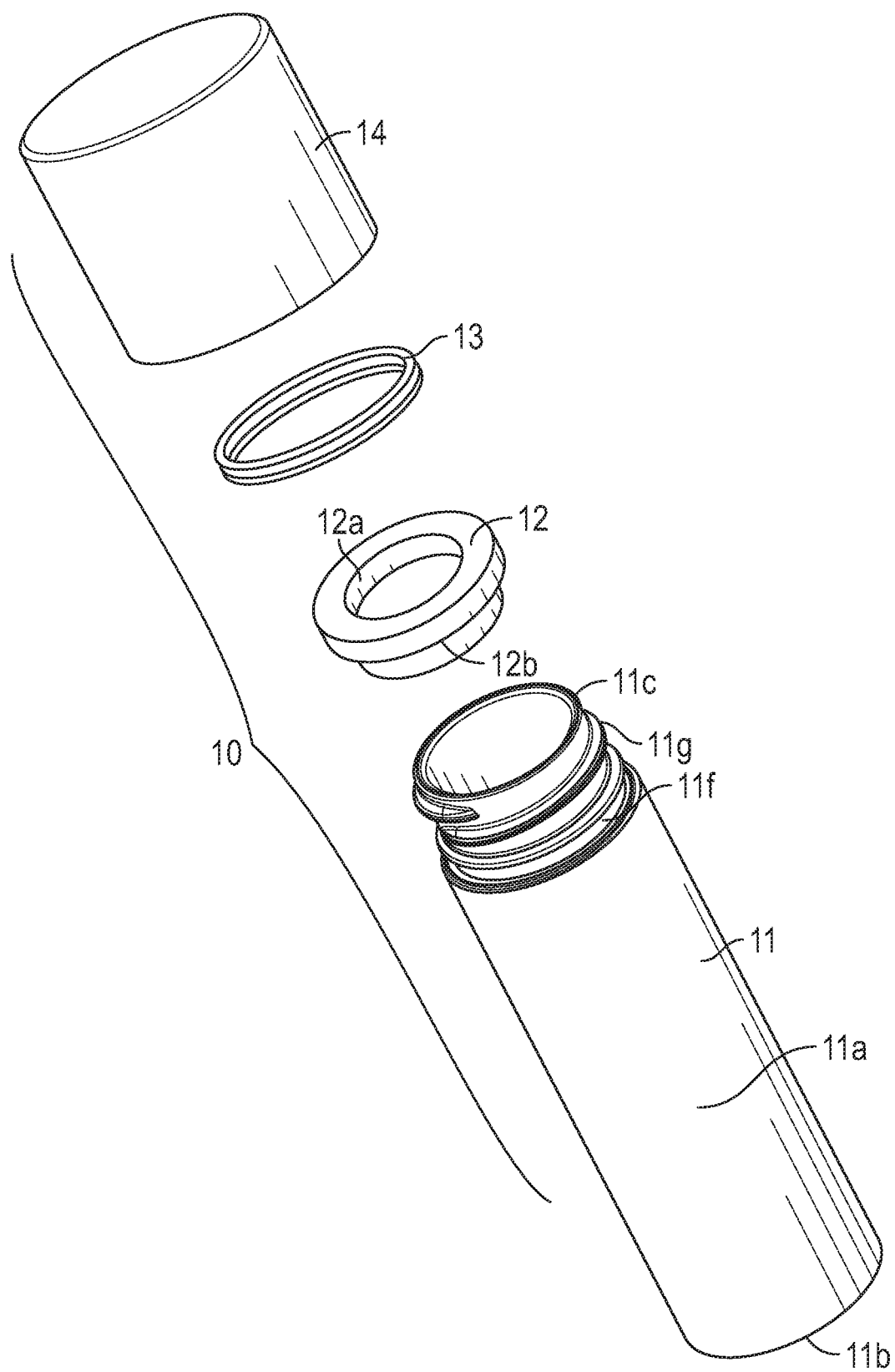
FIG. 1 is an exploded perspective view of a first embodiment of a protective container for a sterilized medical implant in accordance with this invention.

Referring now to the drawings, there is illustrated in FIGS. 1 through 4 a first embodiment of a protective container for a medical implant, indicated generally at 10, in accordance with this invention. As will be explained in detail below, the protective container 10 functions as a sealed enclosure for a sterilized medical implant to protect the medical implant from environmental contaminants and to prevent damage to the medical implant during transport. However, the scope of this invention is not intended to be limited for use with the specific structures of the medical implants described and illustrated or with medical implants in general. On the contrary, as will become apparent below, the protective container 10 of this invention may be used in any desired environment and for any desired purpose.

Figure 2:
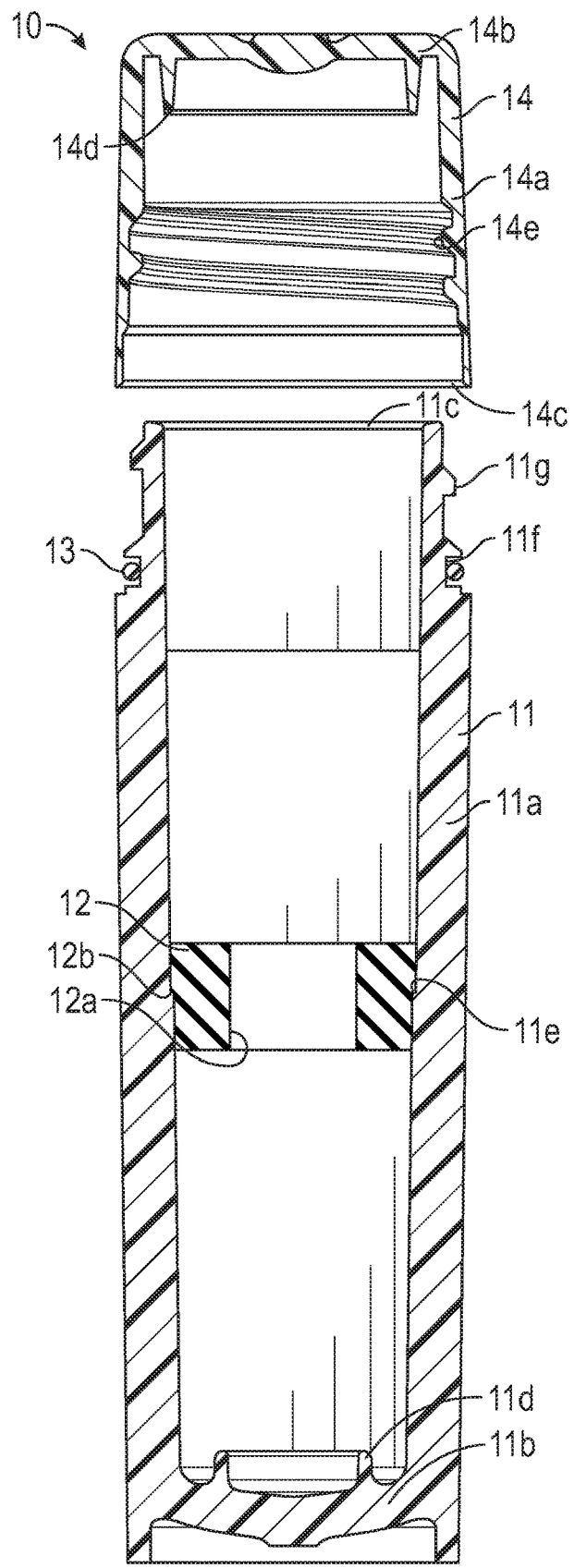
FIG. 2 is a sectional elevational view of the first embodiment of the protective container illustrated in FIG. 1 shown partially assembled.

The first embodiment of the protective container 10 includes a base 11, a stabilizing member 12, a sealing member 13, and a cap 14 that, when assembled together, form a sealed enclosure. The illustrated base 11 is generally hollow and cylindrical shape and includes a body 11a that extends from a closed end 11b to an opened end 11c. However, the base 11 may have any desired shape. As shown in FIG. 2, the closed end 11b of the base 11 has a support structure 11d provided on an interior surface thereof. In the illustrated embodiment, the support structure 11d is an annular ridge that is formed integrally with the closed end 11b of the base 11. However, the support structure 11d may have any desired shape and may be provided at any desired location on the base 11. An internal shoulder 11e is provided on an inner surface of a central region of the body 11a of the base 11. Near the opened end 11c, an annular groove 11f is provided on the outer surface of the base 11 adjacent to the body 11a thereof, and an external thread 11g is provided on the outer surface of the base 11 adjacent to the annular groove 11f. The purposes for the support structure 11d, the internal shoulder 11e, the annular groove 11f, and the external thread 11g will be explained below. The base 11 is preferably formed from a rigid plastic material, although any desired material may be utilized.

The illustrated stabilizing member 12 is annular in shape and has an internal opening 12a and an external shoulder 12b provided thereon. However, the stabilizing member 12 may have any desired shape. The stabilizing member 12 is preferably formed from a resilient elastomeric material, such as rubber, although any material may be utilized. The illustrated sealing member 13 is also annular in shape, although such is not required. The sealing member 13 is also preferably formed from a resilient elastomeric material, such as rubber, although any material may be utilized. The purposes for the stabilizing member 12 and the sealing member 13 will be explained below.

Figure 3:
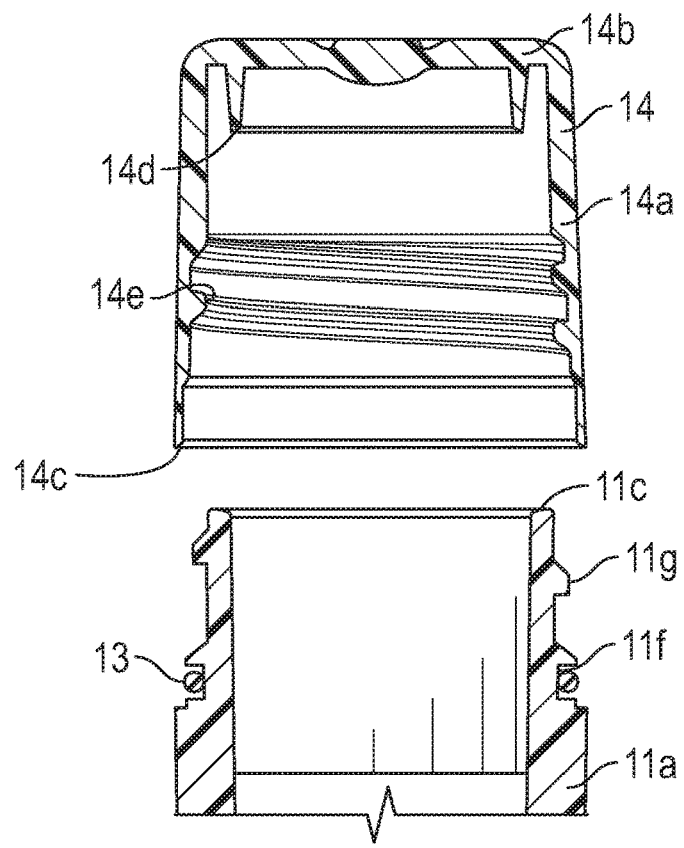
FIG. 3 is an enlarged sectional elevational view of a portion of the first embodiment of the protective container illustrated in FIGS. 1 and 2.
Figure 4:
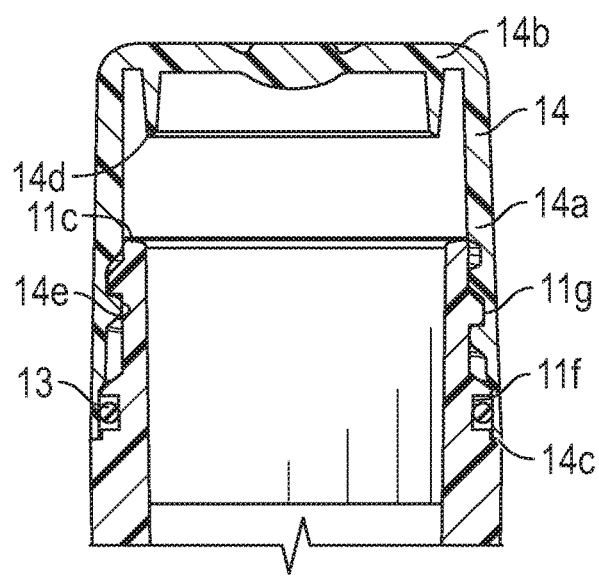
FIG. 4 is an enlarged sectional elevational view of the portion of the first embodiment of the protective container illustrated in FIG. 3 shown assembled.

The illustrated cap 14 is generally hollow and cylindrical shape and includes a body 14a that extends from a closed end 14b to an opened end 14c. However, the cap 14 may have any desired shape. As shown in FIGS. 2 through 4, the closed end 14b of the cap 14 has a support structure 14d provided on an interior surface thereof. In the illustrated embodiment, the support structure 14d is an annular ridge that is formed integrally with the closed end 14b of the cap 14. However, the support structure 14d may have any desired shape and be provided at any desired location on the cap 14. An internal thread 14e is provided on the cap 14 adjacent to the opened end 14c. The purposes for the support structure 14d and the internal thread 14e will be explained below. The cap 14 is also preferably formed from a rigid plastic material, although any desired material may be utilized.

The first embodiment of the protective container 10 may be assembled by initially inserting the stabilizing member 12 within the base 11. To accomplish this, the stabilizing member 12 may be moved axially through the opened end 11c and into the interior of the base 11 until the external shoulder 12b provided on the stabilizing member 12 engages the internal shoulder 11e provided on the base 11, as shown in FIG. 2. Preferably, the outer surface of the stabilizing member 12 is sized to frictionally engage the inner surface of the base 11 when positioned as shown in FIG. 2, although such is not required. Thus, the stabilizing member 12 is positively positioned within and retained on the base 11.

Next, the sealing member 13 is inserted within the annular groove 11f provided about the opened end 11c of the base 11. To accomplish this, the sealing member 13 may be moved axially over the external thread 11g and into the groove 11f, as shown in FIG. 2. Preferably, the sealing member 13 is sized to be received within the groove 11f in a snap-fit relationship, although such is not required. Thus, the sealing member 13 is positively positioned within and retained on the groove 11f.

Lastly, the cap 14 is installed on the base 11 to complete the first embodiment of the protective container 10. To accomplish this, the cap 14 is initially axially aligned with the base 11 such that the external thread 11g provided on the base 11 is located adjacent to the internal thread 14e provided on the cap 14, as shown in FIGS. 2 and 3. The cap 14 is then moved axially relative to the body 11 such that the internal thread 14e engages the external thread 11g. Then, the cap 14 is rotated relative to the body 11. Because of the engagement of the external thread 11g and the internal thread 14e, such rotation causes the cap 14 to move further axially relative to the body 11 to the final orientation shown in FIG. 4. During such movement toward this final orientation, the opened end 14c of the cap 14 is moved axially over the groove 11f containing the sealing member 13. Preferably, the sealing member 13 defines an outer diameter that is somewhat larger than an inner diameter defined by the inner surface of the opened end 14c of the cap 14. Thus, when the cap 14 is located in this final orientation relative to the body 11, the sealing member 13 is compressed radially inwardly by the inner surface of the opened end 14c of the cap 14. Consequently, the interior of the first embodiment of the protective container 10 is positively sealed to prevent the entry of contaminants therein.

As discussed above and shown in FIG. 2, the support structure 11d is formed integrally with the body 11, and the support structure 14d is formed integrally with the cap 14. However, if desired, either or both of these support structures 11d and 14d may be formed as separate components from the body 11 and the cap 14. Additionally, either or both of these support structures 11d and 14d may be embodied as a storage device for the sterilized medical implant, as described below. Also, although the first embodiment of the protective container 10 illustrated in FIGS. 1 through 4 includes both the support structure 11d provided on the body 11 and the support structure 14d provided on the cap 14, this invention contemplates that either, or both, of these support structures 11d and 14d may be omitted.

Figures 5, 6:
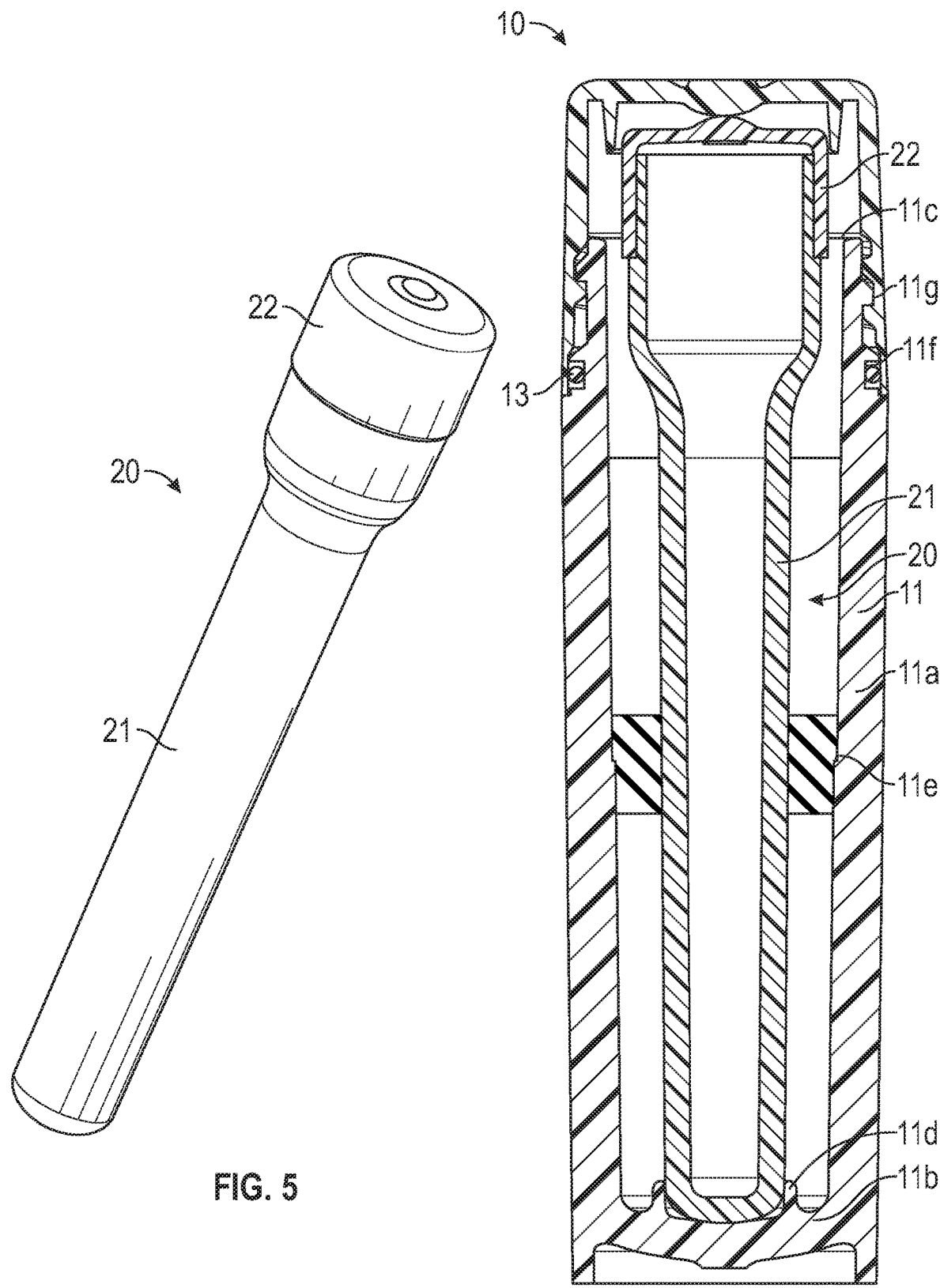
FIG. 5 is a perspective view of a first embodiment of a storage device that may be used with the first embodiment of the protective container illustrated in FIGS. 1 through 4.
FIG. 6 is a sectional elevational view of the first embodiment of the storage device illustrated in FIG. 5 shown supported within the first embodiment of the protective container illustrated in FIGS. 1 through 4.

FIG. 5 illustrates a first embodiment of a storage device, indicated generally at 20, that may be used in conjunction with the first embodiment of the protective container 10 illustrated in FIGS. 1 through 4. The first embodiment of the storage device 20 is a closed container for supporting a sterilized medical implant (not shown) therein. The first embodiment of the storage device 20 is generally hollow and cylindrical in shape (although such is not required) and includes an elongated hollow body portion 21 having a cap portion 22 removably supported thereon. The end of the elongated body portion 21 that is opposite the removable cap portion 22 is preferably sized and shaped to be received within the support structure 11d of the base 11 of the first embodiment of the protective container 10, as shown in FIG. 6. Similarly, the removable cap portion 22 is preferably sized and shaped to be received within the support structure 14d of the cap 14 of the first embodiment of the protective container 10, as also shown in FIG. 6.

The first embodiment of the storage device 20 (containing a sterilized medical implant that is not shown) may be supported within the first embodiment of the protective container 10 as shown in FIG. 6. To accomplish this, the stabilizing member 12 and the sealing member 13 are initially disposed within the body 11a of the base 11 as described above. Then, the first embodiment of the storage device 20 is inserted axially through the opened end 11c and into the interior of the base 11. As a result, the end of the elongated body portion 21 is moved axially through the opening 12a of the stabilizing device 12 into engagement with the support structure 11d of the base 11 of the first embodiment of the protective container 10. Thus, the end of the elongated body portion 21 is received within and positively supported on the support structure 11d of the base 11 of the first embodiment of the protective container 10.

At the same time, a central region of the elongated body portion 21 extends through the opening 12a of the stabilizing device 12. Although not required, the central region of the elongated body portion 21 of the first embodiment of the storage device 20 is preferably sized and shaped to be engaged by an inner surface of the stabilizing device 12 that is defined by the opening 12a. Thus, the central region of the elongated body portion 21 of the first embodiment of the storage device 20 is received within and positively supported on the stabilizing device 12.

Lastly, the cap portion 14 is threaded onto the opened end 11c of the body 11, as described above. Although not required, the cap portion 22 of the first embodiment of the storage device 20 is preferably sized and shaped to be engaged by the support structure 14d of the cap 14, as shown in FIG. 6. Thus, the cap portion 22 of the first embodiment of the storage device 20 is received within and positively supported on the support structure 14d of the cap 14 of the first embodiment of the protective container 10. Because (1) the end of the elongated body portion 21 is received within and positively supported on the support structure 11d of the base 11, (2) the central region of the elongated body portion 21 is received within and positively supported on the stabilizing device 12, and (3) the cap portion 22 is received within and positively supported on the support structure 14d of the cap 14, it can be seen that the first embodiment of the storage device 20 is firmly supported within the first embodiment of the protective container 10 so as to prevent relative movement therebetween. However, the first embodiment of the storage device 20 may be quickly and easily removed from the first embodiment of the protective container 10 when it is desired to retrieve the sterilized medical implant from the interior of the first embodiment of the storage device 20.

It will be appreciated that either, or both, of the support structures 11d and 14d may be embodied as geometric elongations or by appropriately sizing the outer components (i.e., the body 11 and the cap 14) and the inner components (i.e., the storage device 20 or the sterilized medical device itself) such that there is limited or no axial motion permitted. For example, the storage device 20 or the sterilized medical device itself can be snugly fitted to the top and bottom, or circumferentially, of the first embodiment of the protective container 10. Additionally, portions of the body 11 and/or the cap 14 may be provided with identifying characteristics, such as see-through transparency and translucent color-coding or tinting, to facilitate the identification of the sterilized medical device contained therein.

FIGS. 5 and 6 illustrate that a single storage device 20 may be supported within the first embodiment of the protective container 10. It will be appreciated, however, that a plurality of such storage devices 20 may be supported within the first embodiment of the protective container 10. For example, two or more of such storage devices 20 may be supported within the protective container 10 axially adjacent to one another. In such an instance, a first one of the plurality of storage devices 20 may be supported on the support structure 11d provided on the base 11, while a second one of the plurality of storage devices 20 may be supported on the support structure 14d provided on the cap 14. The first and second ones of the plurality of storage devices 20 may axially abut one another to prevent movement relative to the first embodiment of the protective container 10. Alternatively, a first one of the plurality of storage devices 20 may be supported on both the support structure 11d provided on the base 11 and the support structure 14d provided on the cap 14, and a second one of the plurality of storage devices 20 may be supported within the first one of the plurality of storage devices 20, similar to Matryoshka or Russian nesting dolls. Any number of such nested storage devices 20 may be supported in this manner within the first embodiment of the protective container 10.

FIG. 7 illustrates a second embodiment of a storage device, indicated generally at 30, that may be used in conjunction with the first embodiment of the protective container 10 illustrated in FIGS. 1 through 4 for supporting a sterilized medical implant MD therein. The second embodiment of the storage device 30 includes a body portion 31 having first and second support portions 32 and 33 provided therein. The illustrated body portion 31 is formed from a panel of material (such as plastic or cardboard, for example) that is generally flat and rectangular in shape, although such is not required. Each of the illustrated first and second support portions 32 and 33 is generally semicircular in shape and is formed by cutting and bending a portion of the body portion 31 so that it extends generally perpendicular thereto. Each of the illustrated first and second support portions 32 and 33 has an aperture 32a and 33a, respectively, extending therethrough. However, the first and second support portions 32 and 33 may be formed having any desired shapes or combination of shapes. Also, the body portion 31 of the second embodiment of the storage device 30 may have either a greater or lesser number of such support portions 32 and 33 provided thereon.

As shown in FIGS. 7 and 8, the sterilized medical implant MD may be supported on the body portion 31 of the second embodiment of the storage device 30 by inserting it through the respective apertures 32a and 33a of the first and second support portions 32 and 33. In order to retain the sterilized medical implant MD on the body portion 31, the apertures 32a and 33a may be formed having sizes that are slightly smaller than the sizes of the portions of the sterilized medical implant MD extending therethrough. Alternatively, the apertures 32a and 33a may be slightly misaligned relative to the sterilized medical implant MD extending therethrough.

The second embodiment of the storage device 30 may be supported within the first embodiment of the protective container 10 as shown in FIG. 8. To accomplish this, the sealing member 13 is initially disposed within the groove 11f of the base 11 as described above (the stabilizing member 12 may be omitted in this embodiment). Then, the second embodiment of the storage device 30 is inserted axially through the opened end 11c and into the interior of the base 11. As a result, the end of the body portion 31 is moved axially into engagement with the support structure 11d of the base 11 of the first embodiment of protective container 10. Thus, the end of the elongated body 21 may be received within and positively supported on the support structure 11d of the base 11 of the first embodiment of protective container 10.

Lastly, the cap portion 14 is threaded onto the opened end 11c of the body 11, as described above. Although not required, the upper end of the body portion 31 of the second embodiment of the storage device 30 is preferably sized and shaped to be engaged by the support structure 14d of the cap 14, as shown in FIG. 8. Thus, the upper end of the body portion 31 of the second embodiment of the storage device 30 is received within and positively supported on the support structure 14d of the cap 14 of the first embodiment of the protective container 10.

Because the lower end of the body portion 31 is positively supported on the support structure 11d of the base 11 and the upper end of the body portion 31 is positively supported on the support structure 14d of the cap 14, it can be seen that the second embodiment of the storage device 30 is firmly supported within the first embodiment of the protective container 10 so as to prevent relative movement therebetween. However, the second embodiment of the storage device 30 may be quickly and easily removed from the first embodiment of the protective container 10 when it is desired to retrieve the sterilized medical implant MD from the second embodiment of the storage device 30.

FIG. 9 illustrates a third embodiment of a storage device, indicated generally at 40, that may be used in conjunction with the first embodiment of the protective container 10 illustrated in FIGS. 1 through 4 for supporting a sterilized medical implant MD therein. The third embodiment of the storage device 40 includes a body portion 41 having first and second support portions 42 and 43 provided therein. The illustrated body portion 41 is formed from an elongated cylindrical post, although such is not required. Each of the illustrated first and second support portions 42 and 43 is shaped generally in the form of a cylindrical disc, although again such is not required. The illustrated first support portion 42 has a pair of apertures (not shown) extending therethrough. However, the first support portion 42 may be formed having a greater or lesser number of such apertures, and the second support portion 43 may be formed having one or more similar apertures if desired.

As shown in FIGS. 9 and 10, a pair of sterilized medical implants MD may be supported on the body portion 41 of the third embodiment of the storage device 40 by inserting them through the respective apertures of the first support portion 42. In order to retain the sterilized medical implants MD on the body portion 41, the apertures may be formed having sizes that are slightly smaller than the sizes of the sterilized medical implants MD extending therethrough.

The third embodiment of the storage device 40 may be supported within the first embodiment of the protective container 10 as shown in FIG. 10. To accomplish this, the sealing member 13 is initially disposed within the groove 11f of the base 11 as described above (the stabilizing member 12 may be omitted in this embodiment). Then, the third embodiment of the storage device 40 is inserted axially through the opened end 11c and into the interior of the base 11. As a result, the second support portion 43 of the body portion 41 is moved axially into engagement with the support structure 11d of the base 11 of the protective container 10. Thus, the second support portion 43 may be received within and positively supported on the support structure 11d of the base 11 of the first embodiment of the protective container 10.

At the same time, the first support portion 42 of the body portion 41 is disposed within the interior of the base 11. The outer surface of the first support portion 42 is sized to fit snugly within the inner surface of the interior of the base 11, as shown in FIG. 10. Such engagement of the outer surface of the first support portion 42 with the inner surface of the interior of the base 11 prevents or minimizes lateral movement of the third embodiment of the storage device 40 relative to the first embodiment of the protective container 10.

Lastly, the cap portion 14 is threaded onto the opened end 11c of the body 11, as described above. Although not required, the upper end of the body portion 41 of the third embodiment of the storage device 40 is preferably sized and shaped to be engaged by the support structure 14d of the cap 14, as shown in FIG. 10. Thus, the upper end of the body portion 41 of the third embodiment of the storage device 40 is received within and positively supported on the support structure 14d of the cap 14 of the first embodiment of the protective container 10.

Because (1) the second support portion 43 of the body portion 41 is positively supported on the support structure 11d of the base 11, (2) the first support portion 42 of the body portion 41 engages the inner surface of the interior of the base 11, and (3) the upper end of the body portion 41 is positively supported on the support structure 14d of the cap 14, it can be seen that the third embodiment of the storage device 40 is firmly supported within the first embodiment of the protective container 10 so as to prevent relative movement therebetween. However, the third embodiment of the storage device 40 may be quickly and easily removed from the first embodiment of the protective container 10 when it is desired to retrieve the sterilized medical implant MD from the third embodiment of the storage device 40.

Figure 11:
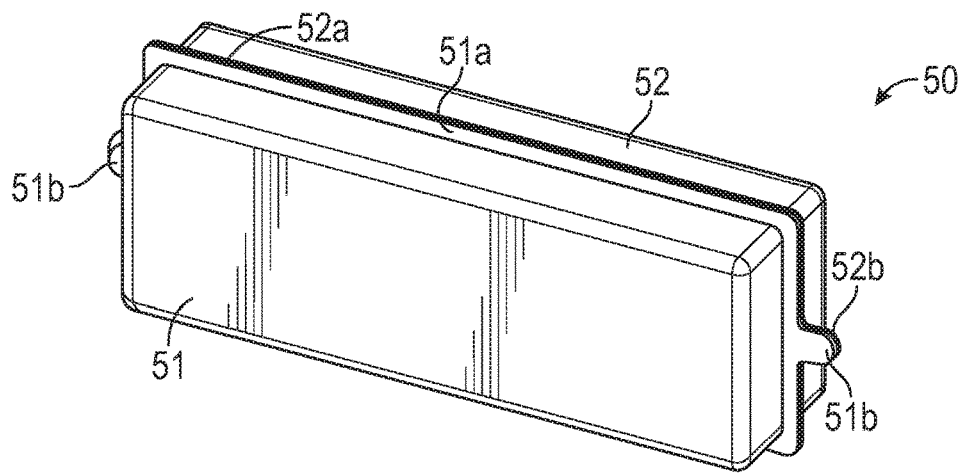
FIG. 11 is a perspective view of a fourth embodiment of a storage device that may be used with the first embodiment of the protective container illustrated in FIGS. 1 through 4.
Figure 12:
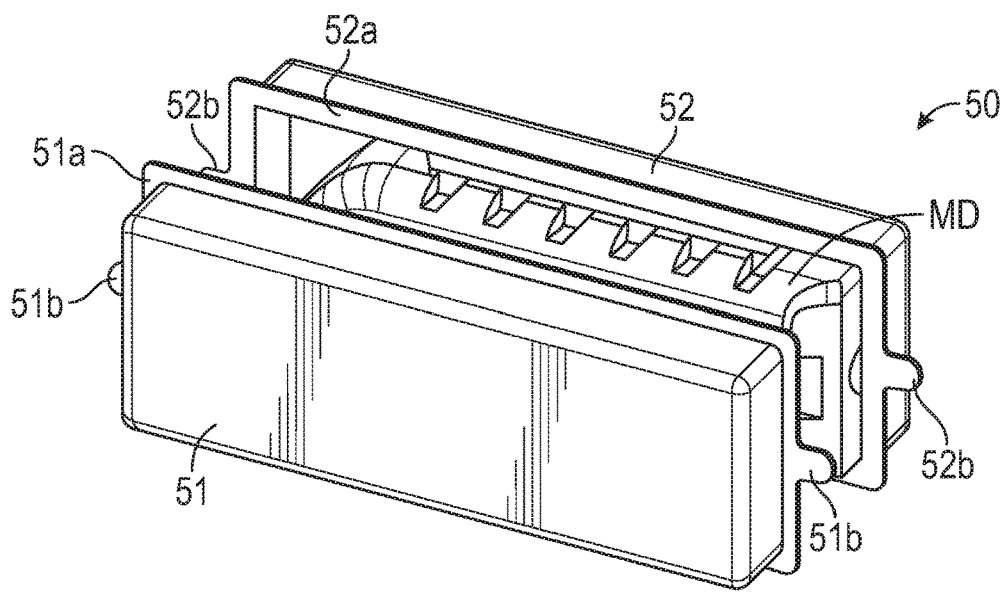
FIG. 12 is an exploded perspective view of the fourth embodiment of the storage device illustrated in FIG. 11.
Figure 13:
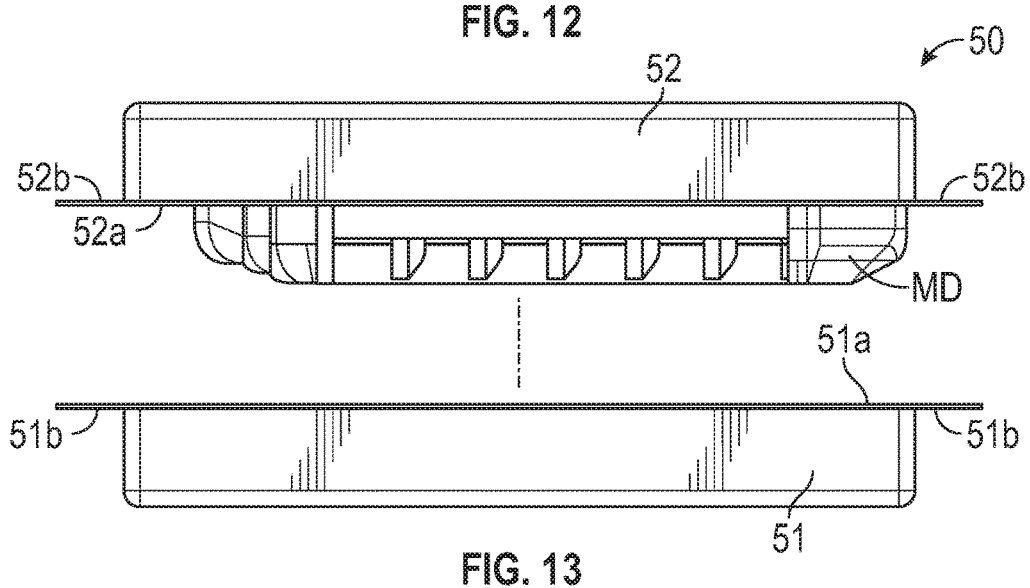
FIG. 13 is an exploded elevational view of the fourth embodiment of the storage device illustrated in FIGS. 11 and 12.
Figure 16:
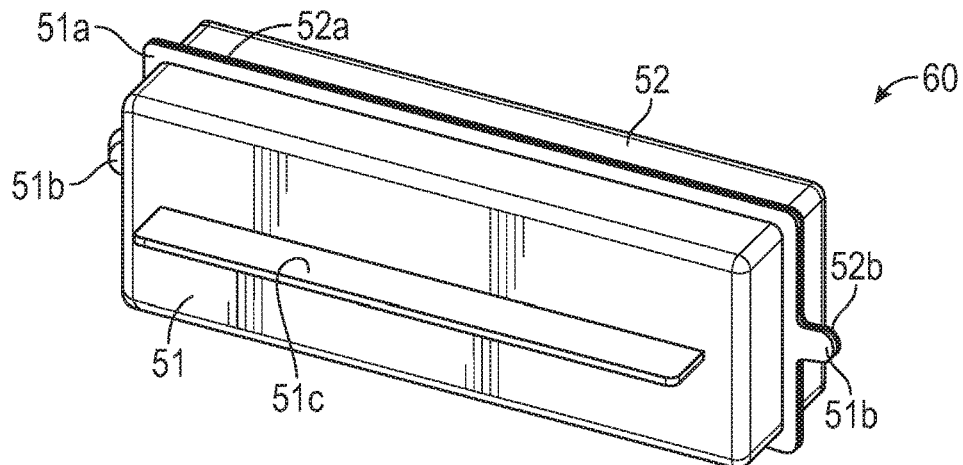
FIG. 16 is a perspective view of a fifth embodiment of a storage device that may be used with the first embodiment of the protective container illustrated in FIGS. 1 through 4.
Figure 17:
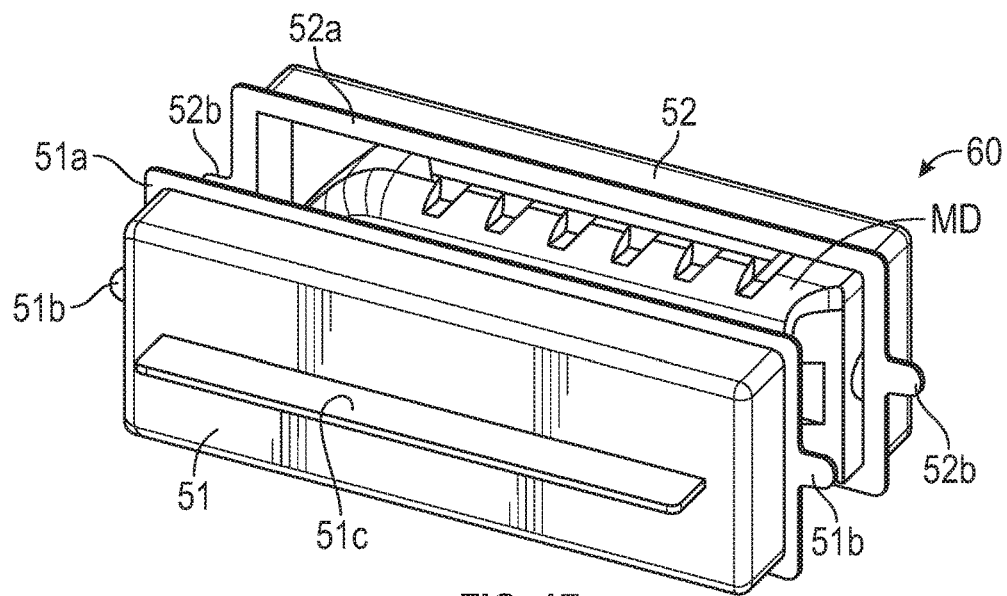
FIG. 17 is an exploded perspective view of the fifth embodiment of the storage device illustrated in FIG. 16.
Figure 18:
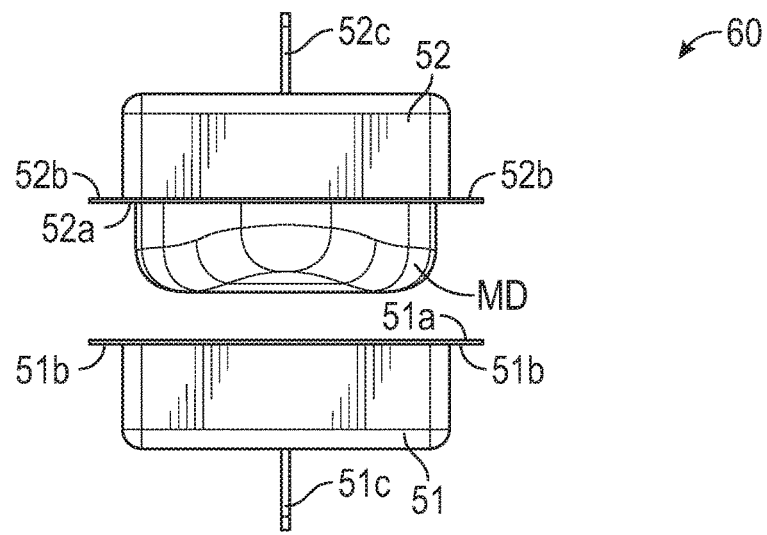
FIG. 18 is an exploded elevational view of the fifth embodiment of the storage device illustrated in FIGS. 16 and 17.

FIGS. 11 through 15 illustrate a fourth embodiment of a storage device, indicated generally at 50, that may be used in conjunction with the first embodiment of the protective container 10 illustrated in FIGS. 1 through 4 for supporting a sterilized medical implant MD therein. The illustrated fourth embodiment of the storage device 50 is shaped generally in the form of a rectangular parallelepiped, although such is not required. The fourth embodiment of the storage device 50 includes first and second cup-shaped body portions 51 and 52 that cooperate to define an interior space within which the sterilized medical implant MD may be disposed, as shown in FIGS. 12 and 13. The first body portion 51 has a flange 51a extending about the opened end thereof. At opposed ends of the first body portion 51, the flange 51a has an extended portion 51b. Similarly, the second body portion 52 has a flange 52a extending about the opened end thereof. At opposed ends of the second body 52, the flange 52a has an extended portion 52b. The purposes of the flanges 51a and 52a and the associated extended portions 51b and 52b will be explained below.

In use, the sterilized medical implant MD is initially disposed within the interior of the second body portion 52 of the fourth embodiment of the storage device 50, as shown in FIGS. 12 and 13. Then, the first body portion 51 is moved into engagement with the second body portion 52, as shown in FIG. 11. In this orientation, the flanges 51a and 52a (including the respective extended portions 51b and 52b) are disposed adjacent to and engage one another. If desired, a retaining structure (not shown) may be provided to positively retain the first and second body portions 51 and 52 in this orientation.

The fourth embodiment of the storage device 50 may be supported within the first embodiment of the protective container 10 as shown in FIGS. 14 and 15. To accomplish this, the sealing member 13 is initially disposed within the groove 11f of the base 11 as described above (the stabilizing member 12 may be omitted in this embodiment). Then, the fourth embodiment of the storage device 50 is inserted axially through the opened end 11c and into the interior of the base 11. As a result, a first pair of the extended portions 51b and 52b are moved axially into engagement with the support structure 11d of the base 11 of the first embodiment of the protective container 10. Thus, the extended portions 51b and 52b may be received within and positively supported on the support structure 11d of the base 11 of the first embodiment of the protective container 10.

At the same time, the flanges 51a and 52a are disposed within the interior of the base 11. The outer surfaces of the flanges 51a and 52a are sized to fit snugly within the inner surface of the interior of the base 11, as shown in FIGS. 14 and 15. Such engagement of the flanges 51a and 52a with the inner surface of the interior of the base 11 prevents or minimizes lateral movement of the fourth embodiment of the storage device 50 relative to the first embodiment of the protective container 10.

Lastly, the cap portion 14 is threaded onto the opened end 11c of the body 11, as described above. Although not required, a second pair of the extended portions 51b and 52b of the fourth embodiment of the storage device 50 is preferably sized and shaped to be engaged by the support structure 14d of the cap 14, as shown in FIG. 14. Thus, the upper end of the fourth embodiment of the storage device 50 is received within and positively supported on the support structure 14d of the cap 14 of the protective container 10. Thus, the fourth embodiment of the storage device 50 is firmly supported within the first embodiment of the protective container 10 so as to prevent relative movement therebetween. However, the fourth embodiment of the storage device 50 may be quickly and easily removed from the first embodiment of the protective container 10 when it is desired to retrieve the sterilized medical implant MD from the fourth embodiment of the storage device 50.

FIGS. 16 through 20 illustrate a fifth embodiment of a storage device, indicated generally at 60, that may be used in conjunction with the first embodiment of the protective container 10 illustrated in FIGS. 1 through 4 for supporting a sterilized medical implant MD therein. The fifth embodiment of the storage device 60 is, in large measure, identical to the fourth embodiment of the storage device 50 illustrated in FIGS. 11 through 15, and like reference numbers are used to indicate similar components. However, the fifth embodiment of the storage device 60 further includes a first positioning fin 51c that is provided on the first body portion 51 and a second positioning fin 52c that is provided on second body portion 52. The first and second positioning fins 51c and 52c extend generally perpendicularly relative to the respective first and second flanges 51a and 52a, although such is not required. As best shown in FIG. 20, the outer surfaces of the first and second positioning fins 51c and 52c are sized to fit snugly within the inner surface of the interior of the base 11. Similar to the first and second flanges 51a and 52a, the engagement of the first and second positioning fins 51c and 52c with the inner surface of the interior of the base 11 further prevents or minimizes lateral movement of the fifth embodiment of the storage device 60 relative to the first embodiment of the protective container 10.

Figure 21:
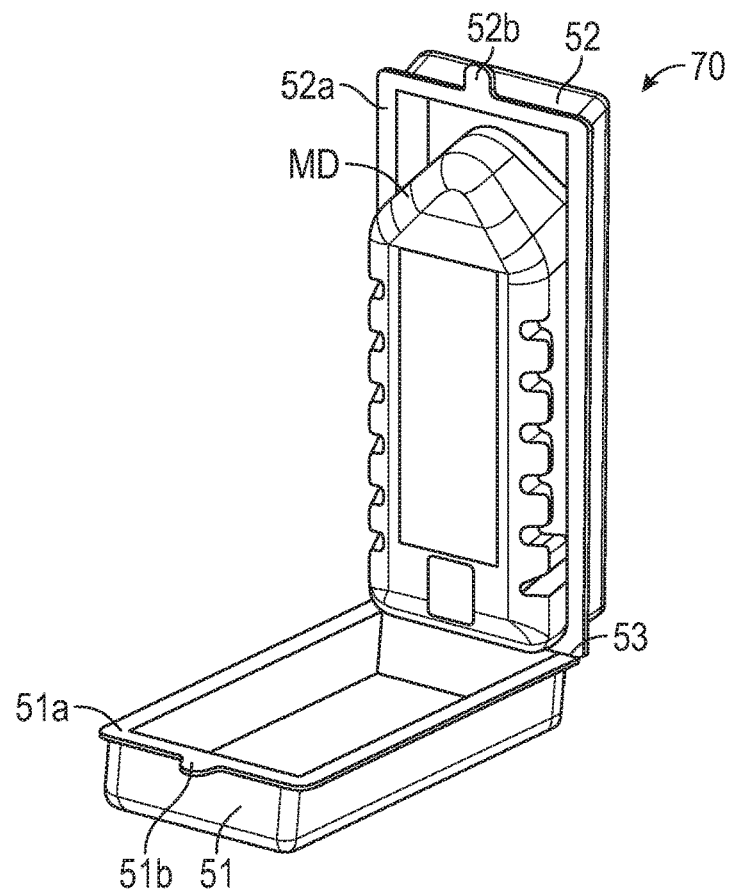
FIG. 21 is a perspective view of a sixth embodiment of a storage device that may be used with the first embodiment of the protective container illustrated in FIGS. 1 through 4.

FIG. 21 illustrates a sixth embodiment of a storage device, indicated generally at 70, that may be used in conjunction with the first embodiment of the protective container 10 illustrated in FIGS. 1 through 4 for supporting a sterilized medical implant MD therein. The sixth embodiment of the storage device 70 is, in large measure, identical to the fourth embodiment of the storage device 50 illustrated in FIGS. 11 through 15, and like reference numbers are used to indicate similar components. However, the sixth embodiment of the storage device 70 further includes a hinge 53 that pivotably connects the first body portion 51 to the second body portion 52. This clamshell-type arrangement may facilitate handling and use of the sixth embodiment of the storage device 70.

Figure 22:
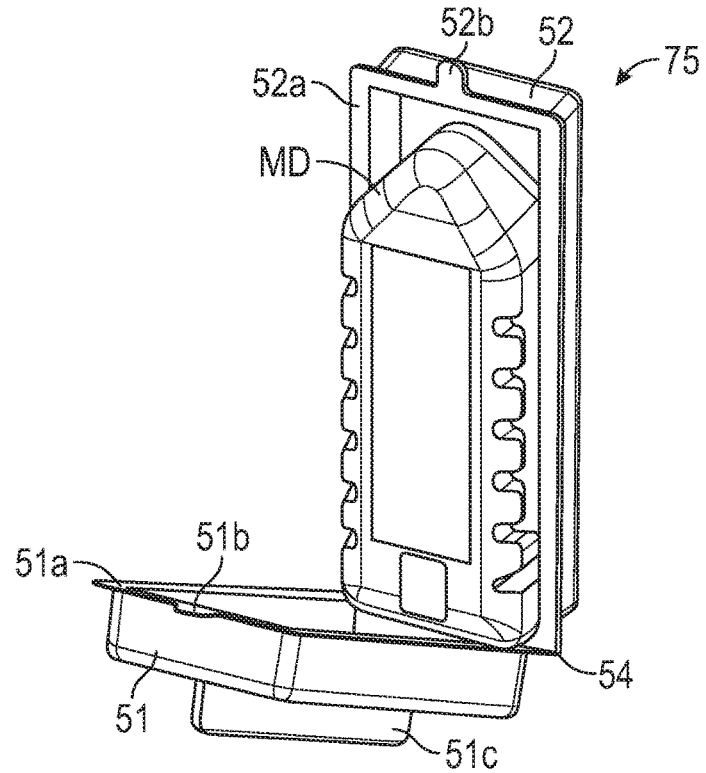
FIG. 22 is a perspective view of a seventh embodiment of a storage device that may be used with the first embodiment of the protective container illustrated in FIGS. 1 through 4.

FIG. 22 illustrates a seventh embodiment of a storage device, indicated generally at 75, that may be used in conjunction with the first embodiment of the protective container 10 illustrated in FIGS. 1 through 4 for supporting a sterilized medical implant MD therein. The seventh embodiment of the storage device 75 is, in large measure, identical to the fifth embodiment of the storage device 60 illustrated in FIGS. 16 through 20, and like reference numbers are used to indicate similar components. However, the seventh embodiment of the storage device 75 further includes a hinge 54 that pivotably connects the first body portion 51 to the second body portion 52. This clamshell-type arrangement may facilitate handling and use of the seventh embodiment of the storage device 75.

Figure 23:
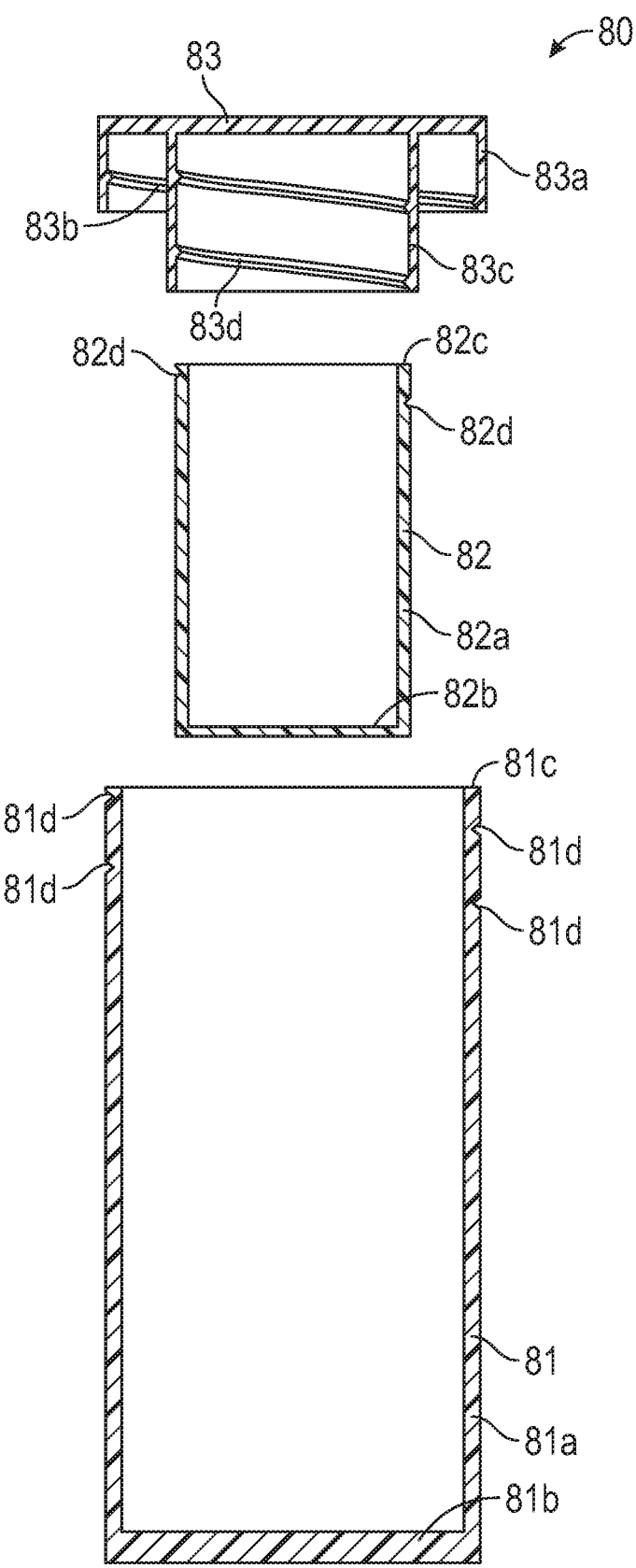
FIG. 23 is an exploded elevational view of a second embodiment of a protective container in accordance with this invention.

FIG. 23 illustrates a second embodiment of a protective container, indicated generally at 80. The second embodiment of the protective container 80 includes an outer container portion 81, an inner container portion 82, and a cap portion 83. The illustrated outer container portion 81 is generally hollow and cylindrical in shape and includes a body 81a that extends from a closed end 81b to an opened end 81c. However, the outer container portion 81 may have any desired shape. An external thread 81d is provided on the outer surface of the body 81a adjacent to the opened end 81c. Similarly, the inner container portion 82 is generally hollow and cylindrical in shape and includes a body 82a that extends from a closed end 82b to an opened end 82c. However, the inner container portion 82 may have any desired shape. An external thread 82d is provided on the outer surface of the body 82a adjacent to the opened end 82c.

The illustrated cap portion 83 includes a generally circular end wall having an outer skirt 83a depending therefrom. The illustrated outer skirt 83a is generally hollow and cylindrical in shape (although such is not required) and has an internal thread 83b provided thereon. The internal thread 83b provided on the outer skirt 83a is sized and shaped to cooperate with the external thread 81d provided on the outer surface of the body 81a of the outer container portion 81. Thus, the outer container portion 81 can be releasably secured to the outer skirt 83*a* of the cap portion 83. Similarly, the circular end wall of the illustrated cap portion 83 also has an inner skirt 83*c* depending therefrom. The illustrated inner skirt 83*c* is generally hollow and cylindrical in shape (although such is not required) and has an internal thread 83*d* provided thereon. The internal thread 83*d* provided on the inner skirt 83*c* is sized and shaped to cooperate with the external thread 82*d* provided on the outer surface of the body 82*a* of the inner container portion 82. Thus, the inner container portion 82 can be releasably secured to the inner skirt 83*c* of the cap portion 83.

In use, a sterilized medical implant (not shown) is disposed within the inner container portion 82. Then, the inner container portion 82 is threaded onto the inner skirt 83*c* of the cap portion 83 to retain the sterilized medical implant contained therein in a sterile environment. Next, the outer container portion 81 is threaded onto the outer skirt portion 83*a* of the cap portion 83 to protectively cover the inner container portion 82 and the sterilized medical implant contained therein. To remove the sterilized medical implant for use, these steps are reversed.

FIGS. 24 and 25 illustrate a third embodiment of a protective container, indicated generally at 90, in accordance with this invention. The third embodiment of the protective container 90 includes a body 91 that is generally hollow and cylindrical in shape, extending from a closed end 92 to an opened end 93. A lid 94 is pivotably retained on the opened end 93 of the third embodiment of the protective container 90 by a hinge 95 or by any other conventional structure. Alternatively, the lid 94 may not be retained on the opened end 93. The lid 94 further includes a pull tab 96 extending therefrom. The illustrated pull tab 96 includes an opening 96*a* to facilitate grasping and pulling of the pull tab 96 to move the lid 94 from a closed position (illustrated in FIG. 24) to an opened position (illustrated in FIG. 25) relative to the body 91.

In use, the lid 94 is initially in the opened position relative to the body 91, allowing a sterilized medical implant (not shown) to be inserted within the body 91. Then, the lid 94 is moved to the closed position and sealed about the opened end 93 of the body 91. Thus, the sterilized medical implant is protectively contained within the third embodiment of the protective container 90 until needed for use. When that time arrives, the pull tab 96 is grasped and pulled so as to move the lid 94 from the closed position to the opened position, thereby allowing access to the sterilized medical implant contained within the body 91.

Figures 26, 27:
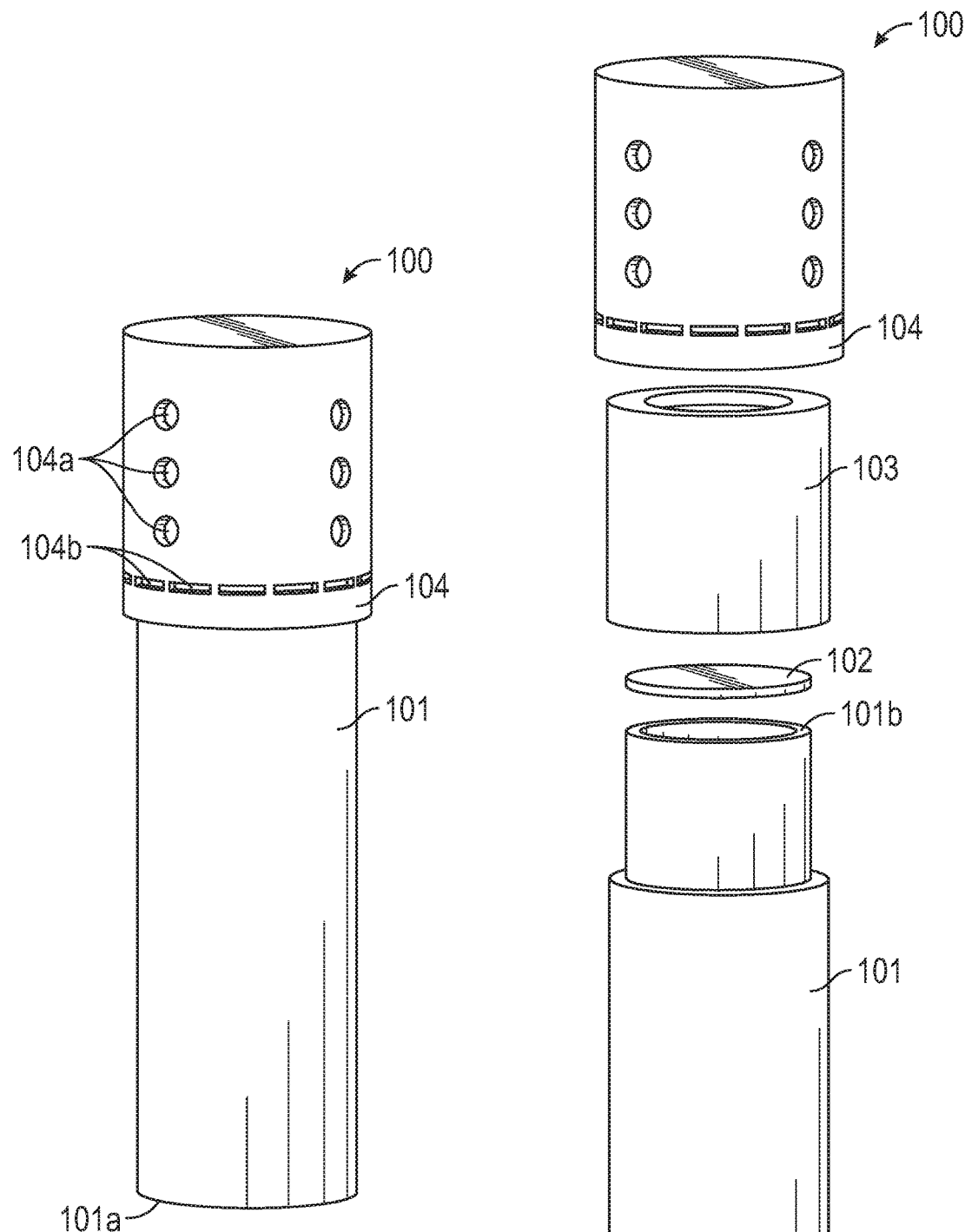
FIG. 26 is a perspective view of a fourth embodiment of a protective container in accordance with this invention.
FIG. 27 is an exploded perspective view of the fourth embodiment of the protective container illustrated in FIG. 26.

FIGS. 26 and 27 illustrate a fourth embodiment of a protective container, indicated generally at 100, in accordance with this invention. The fourth embodiment of the protective container 100 includes a body 101, a seal 102, a closure 103, and an anti-tamper barrier 104. The illustrated body 101 is generally hollow and cylindrical in shape, including an interior that extends from a closed end 101*a* to an opened end 101*b*. However, the body 101 may have any desired shape. The interior of the body 101 is adapted to support a sterilized medical implant (not shown) therein. After the sterilized medical implant has been disposed within the interior of the body 101, the seal 102 is secured to the opened end 101*b* of the body 101. The seal 102 may be embodied as any conventional sealing structure. Next, the closure 103 is mounted on the body 101 to protectively cover the seal 102.

Lastly, the anti-tamper barrier 104 is mounted on the body 101 so as to extend about the closure 103. The anti-tamper barrier 104 has one or more holes 104*a* extending therethrough that allow a sterilant (such as ethylene oxide, for example) to pass therethrough into the third embodiment of the protective container 100. Preferably, the holes 104*a* are located on the anti-tamper barrier 104 in such a manner as to prevent direct linear access to the seal 102. In the illustrated embodiment, the holes 104*a* extend radially through portions of the anti-tamper barrier 104, while the seal 102 faces axially. Thus, direct linear access through the holes 104*a* to the seal 102 is prevented. If desired, the anti-tamper barrier 104 may additionally have one or more conventional tamper-resistant or tamper-evident structures 104*b* provided thereon.

FIGS. 28, 29, and 30 illustrate a fifth embodiment of a protective container, indicated generally at 110, in accordance with this invention. The fifth embodiment of the protective container 110 includes a body 111, a closure 112 including a seal 113, and an anti-tamper barrier 114. The illustrated body 111 is generally hollow and cylindrical in shape, including an interior that extends from a closed end 111*a* to an opened end 111*b*. However, the body 111 may have any desired shape. The interior of the body 111 is adapted to support a sterilized medical implant (not shown) therein. After the sterilized medical implant has been disposed within the interior of the body 111, the closure 112 (including the seal 113) is secured to the opened end 111*b* of the body 111. The seal 113 may be embodied as any conventional sealing structure. As shown in FIG. 29, the closure 112 has one or more holes 112*a* that allow a sterilant to pass therethrough into the fifth embodiment of the protective container 110. In the illustrated embodiment, four of such holes 112*a* are equidistantly spaced apart from one another along a circumference of a circle having a relatively small diameter. However, any desired number of such holes 112*a* may be provided in any desired arrangement. As shown in FIG. 30, the seal 113 extends over all of the plurality of holes 112*a* extending through the axial face of the closure 112.

Lastly, the anti-tamper barrier 114 is mounted on the closure 112. The anti-tamper barrier 114 has one or more holes 114*a* extending therethrough that also allow the sterilant to pass therethrough into the fifth embodiment of the protective container 110. In the illustrated embodiment, six of such holes 114*a* are equidistantly spaced apart from one another along a circumference of a circle having a relatively large diameter. However, any desired number of such holes 114*a* may be provided in any desired arrangement. Preferably, the holes 114*a* extending through the anti-tamper barrier 114 are not co-axially aligned with the holes 112*a* extending through the closure 112. Thus, direct linear access through the holes 114*a* and the holes 112*a* to the seal 113 is prevented. If desired, the anti-tamper barrier 114 may additionally have one or more conventional tamper-resistant or tamper-evident structures (not shown) provided thereon.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A protective container for a sterilized medical implant comprising:
   a base including a hollow body having a closed end and an opened end;
   a cap that is secured about the opened end of the hollow body;
   a sealing member that is compressed between the cap and the base to provide a seal therebetween; and a first support structure that is provided on the closed end of the base and a second support structure that is provided on the cap that are each adapted to support a sterilized medical implant within the hollow body of the base; wherein:
- the first support structure is an annular ridge that is provided on the closed end of the base;
- the second support structure is an annular ridge that is provided on the cap;
- an internal shoulder is provided on an inner surface of the hollow body of the base;
- an annular stabilizing member is supported on the internal shoulder of the hollow body;
- an annular groove is provided on the base adjacent to the hollow body, and
- the sealing member is disposed within the groove and is radially compressed between the cap and the base.

2. The protective container for a sterilized medical implant defined in claim 1 further including a storage device for a sterilized medical implant disposed within the hollow body of the base.

3. The protective container for a sterilized medical implant defined in claim 2 wherein the storage device includes a first end that is supported on the first support structure and a second end that is supported on the second support structure.

4. The protective container for a sterilized medical implant defined in claim 2 wherein the annular stabilizing member engages the storage device.

5. The protective container for a sterilized medical implant defined in claim 4 wherein the annular stabilizing member includes an opening, and wherein the storage device extends through the opening of the annular stabilizing member.

6. The protective container for a sterilized medical implant defined in claim 2 wherein the storage device includes a first end that is supported on the first support structure and a second end that is supported on the second support structure, and wherein the annular stabilizing member engages the storage device.

7. The protective container for a sterilized medical implant defined in claim 6 wherein the annular stabilizing member includes an opening, and wherein the storage device extends through the opening of the annular stabilizing member.

* * * * *